(12) United States Patent
Glozman et al.

(10) Patent No.: US 11,369,444 B2
(45) Date of Patent: **\*Jun. 28, 2022**

(54) NEEDLE STEERING BY SHAFT MANIPULATION

(71) Applicant: TECHNION RESEARCH & DEVELOPMENT FOUNDATION LTD., Haifa (IL)

(72) Inventors: Daniel Glozman, Kfar Adummim (IL); Gonen Daskal, Kefar Hanassi (IL); Moshe Shoham, Hoshaya (IL); Michael Arad, Tel Aviv (IL); Yoav Pinsky, Beit Keshet (IL)

(73) Assignee: TECHNION RESEARCH & DEVELOPMENT FOUNDATION LIMITED, Haifa (IL)

( \* ) Notice: Subject to any disclaimer, the term of this patent is extended or adjusted under 35 U.S.C. 154(b) by 315 days.

This patent is subject to a terminal disclaimer.

(21) Appl. No.: 16/714,840

(22) Filed: Dec. 16, 2019

(65) Prior Publication Data

US 2020/0179066 A1     Jun. 11, 2020

Related U.S. Application Data

(63) Continuation of application No. 15/027,438, filed as application No. PCT/IL2014/050891 on Oct. 7, 2014, now Pat. No. 10,507,067.

(Continued)

(51) Int. Cl.
*A61B 17/34*     (2006.01)
*A61B 34/30*     (2016.01)
(Continued)

(52) U.S. Cl.
CPC ............. *A61B 34/30* (2016.02); *A61B 90/11* (2016.02); *A61B 90/37* (2016.02);
(Continued)

(58) Field of Classification Search
CPC ... A61B 34/30; A61B 90/11; A61B 2034/304; A61B 90/37; A61B 2090/374; A61B 2090/3762; A61B 2017/3409
See application file for complete search history.

(56) References Cited

U.S. PATENT DOCUMENTS 5,572,999 A   11/1996 Funda et al.
6,400,979 B1   6/2002 Stoianovici et al.
(Continued)

FOREIGN PATENT DOCUMENTS

EP   2561821 A1   2/2013
WO   2006081409 A2   8/2006
WO   2007141784 A2   12/2007

OTHER PUBLICATIONS

J. Hong et al., An ultrasound-driven needle-insertion robot for percutaneous cholecystostomy, Physics in Medicine and Biology, Jan. 16, 2004, p. 441-455, vol. 49, No. 3, IOP Publishing Ltd.

(Continued)

*Primary Examiner* — George J Ulsh
(74) *Attorney, Agent, or Firm* — The Roy Gross Law Firm, LLC; Roy Gross

(57) ABSTRACT

A method and apparatus for steering of a flexible needle into tissue using a steering robotic platform for manipulation of the needle shaft, and by use of a semi-active arm for locating and orienting of the steering robot on the patient's body. As opposed to other steering methods, the robot does not hold the base of the needle, which is its proximal region, but rather grips the shaft of the needle by means of a manipulatable needle gripping device, near its distal end. The needle gripper attached to the robotic platform may be equipped with a traction assembly to provide motion to the needle in its longitudinal direction, such that it co-ordinates the entry of the needle with the desired entry angle. The gripping of (Continued)

the needle at its distal end, close to its insertion point, provides the needle manipulator with a low profile, with concomitant advantages.

18 Claims, 5 Drawing Sheets

Related U.S. Application Data

(60) Provisional application No. 61/887,654, filed on Oct. 7, 2013.

(51) Int. Cl.
  *A61B 90/11* (2016.01)
  *A61B 90/00* (2016.01)

(52) U.S. Cl.
  CPC . *A61B 2017/3409* (2013.01); *A61B 2034/304* (2016.02); *A61B 2090/374* (2016.02); *A61B 2090/3762* (2016.02)

(56) References Cited

U.S. PATENT DOCUMENTS

| | | | |
|---|---|---|---|
| 7,008,373 | B2 | 3/2006 | Stoianovici et al. |
| 7,175,635 | B2 | 2/2007 | Loser |
| 2005/0267359 | A1 | 12/2005 | Hussaini et al. |
| 2006/0229641 | A1 | 10/2006 | Gupta |
| 2007/0016067 | A1 | 1/2007 | Webster et al. |
| 2008/0167663 | A1 | 7/2008 | De Mathelin et al. |
| 2010/0063514 | A1 | 3/2010 | Maschke et al. |
| 2010/0234856 | A1 | 9/2010 | Stoianovici et al. |
| 2011/0264112 | A1 | 10/2011 | Nowlin et al. |

OTHER PUBLICATIONS

International Search Report and Written Opinion of the ISA, PCT/IL2014/050891, dated Feb. 8, 2015.

Melzer, Andreas, Melzer, Andreas, INNOMOTION for Percutaneous Image-Guided Interventions, IEEE Engineering in Medicine and Biology Magazine, p. 66-73, 2008-May/Jun., Digital Object Identifier 10.1109/EMB.2007.910274.

European Supplementary Search Report and Written Opinion, dated Apr. 18, 2017, in EP Patent Application No. 14852135.4 corresponding to U.S. Appl. No. 15/027,438.

Translation of Office Action of the Japanese Patent Office, dated Jul. 10, 2018, in corresponding Japanese patent application No. JP2016521283.

Translation of Office Action of the Chinese Patent Office, dated Aug. 31, 2018, in corresponding Chinese patent application No. 201480066546.5.

Translation of Office Action of the Chinese Patent Office, dated Jan. 11, 2018, in corresponding Chinese patent application No. 201480066546.5.

NEEDLE STEERING BY SHAFT MANIPULATION

CROSS-REFERENCE TO RELATED APPLICATIONS

This application is a Continuation of U.S. patent application Ser. No. 15/027,438 filed Apr. 6, 2016, now U.S. Pat. No. 10,507,067, issued Dec. 17, 2019, which is a U.S. National Phase Application under 35 U.S.C. 371 of International Application No. PCT/IL2014/050891, which has an international filing date of Oct. 7, 2014, and which claims the benefit of priority from U.S. Provisional Patent Application No. 61/887,654, filed Oct. 7, 2013, the disclosures of which are incorporated herein by reference in their entirety.

FIELD OF THE INVENTION

The present invention relates to the field of devices for needle steering and their use in image-guided robotic needle steering.

BACKGROUND OF THE INVENTION

Many routine treatments employed in modern clinical practice involve percutaneous insertion of needles and catheters for biopsy and drug delivery and other therapies. The aim of a needle insertion procedure is to place the tip of an appropriate needle safely and accurately in a target region, which could be a lesion, organ or vessel. Examples of treatments requiring needle insertions include vaccinations, blood/fluid sampling, regional anesthesia, tissue biopsy, catheter insertion, cryogenic ablation, electrolytic ablation, brachytherapy, neurosurgery, deep brain stimulation and various minimally invasive surgeries.

Guidance and steering of needles in soft tissue is a complicated task that requires good 3-D coordination, knowledge of the patient anatomy and a high level of experience. Therefore robotic systems have been proposed for performing these functions. Among such robotic systems are those described in U.S. Pat. No. 7,008,373 to D. Stoianovici, for "System and method for robot targeting under fluoroscopy"; and in U.S. Pat. No. 5,572,999 to Funda et al, for "Robotic system for positioning a surgical instrument relative to a patient's body"; and in the product data sheets on the Innomotion robot, as provided by Innomedic GmbH, of Philippsburg-Rheinsheim, Germany.

All of these systems are guiding systems that help in choosing the insertion point and in aligning the needle with the target. The insertion is then done by the surgeon who pushes the needle along the straight line. Such systems usually work with 3-D data taken before the procedure, typically by CT or MRI. The 3-D reconstruction of the patient anatomy is done first. Then the needle is registered to the 3-D anatomy and the robot can orient a cannula so that it will be aligned with the target. Through that cannula the doctor inserts a needle assuming that the needle will not deviate from a straight line and that it will hit the target. A problem with this method is that both needles and tissue are flexible, and the needle therefore does not always proceed in a straight line even in soft tissue. It may deviate from the planned straight path, and methods are needed for ensuring that it does reach the intended target region.

A method for needle steering which is based on the lateral forces exerted on the tip of flexible beveled needle has been described in published US Patent Application US 2007/0016067 A1 to R. J. Webster III et al, for "Distal Bevel Tip Needle Control Device and Algorithm". This application describes a needle driver which grasps the base of the beveled needle and drives the needle shaft by pushing it for longitudinal entry, and rotating it for steering.

In PCT publication No. WO 2007/141784 to D. Glozman et al, for "Controlled Steering of a Flexible Needle", there is described another method in which the base of the needle is held by a robot, and the needle is steered by manipulation of the needle base by the robot.

However, all of the methods and systems described above use needles gripped robotically or otherwise, at their proximal ends, remote from the insertion point into the patient. This results in the need for a large workspace, which may be especially problematic in the realm of imaging systems, where headroom above the supine patient is often limited. There therefore exists a need for a more compact method of manipulating a needle during the insertion process into a subject.

The disclosures of each of the publications mentioned in this section and in other sections of the specification, are hereby incorporated by reference, each in its entirety.

SUMMARY OF THE INVENTION

The present disclosure describes a method and apparatus for steering of a flexible needle inside soft tissue by manipulation of the needle shaft, and by use of a semi-active device for locating and orienting of the steering robot on the patient's body. As opposed to other steering methods, the robot does not hold the base of the needle, or a proximal point close to the base of the needle, but rather grips the shaft of the needle by its distal part, closer to the insertion point into the patient, by means of a manipulatable needle gripper. The combination of the needle gripper and the robotic platform for manipulating the needle gripper is called in this application, a robotic needle manipulator.

The robotic needle manipulator should be able to move with at least 4 degrees of freedom. The minimal four degrees of freedom enable orientation and positioning of the robotic needle manipulator. Two degrees of freedom are needed for positioning the entry point of the needle and two for orientation. Motion perpendicular to the plane is not essential, since the insertion motion of the needle may be provided by a pushing motion generated within the robotic needle manipulator, as described below. Since the robotic needle manipulator does not have to generate the motion required for insertion of the full length of the needle, which could be considerable, the workspace required by the system is significantly smaller than that of prior art systems which do perform the robotic insertion themselves. However, use of a robotic platform with more than 4 degrees of freedom may also be advantageous, though the use of the direction of freedom in the direction parallel to the needle will not generally be used for inserting the needle, because the large travel generally required for inserting the needle may conflict with the need to maintain a low profile workspace of the robotic needle manipulator.

Besides the needle orientation and positioning functions generated by the robotic actuator, as described above, the robotic needle manipulator should also be able to insert the needle by means of a mechanism which moves the needle in its longitudinal direction. This mechanism can be either a mechanical system designed to grip the needle shaft and to move it inwards and outwards, or alternatively, the "mechanism" could simply be a manual operation by the medical personnel inserting the needle by hand while the gripping action of the robotic needle manipulator is released, or alternatively, not even fitted, with the needle held freely in a cannula.

In addition, rotation of the needle may be useful for use with beveled needle guidance systems, or, simply in order to keep the bevel at 90 degrees to the imaging plane so that if lateral forces develop during the insertion, the deviation generated because of the beveled needle will be in the imaging plane, where imaging is optimal for detection of such a deviation. The proposed system can work with various medical image modes, such as CT, MRI, PET or Ultrasound.

The needle may be inserted either continuously or step by step, requiring operator approval for each step. A major innovative aspect of this system is in the manipulation of the needle by means of its distal portion.

One advantage of the systems described in this application is that the workspace required for the robot is significantly smaller than for prior art systems, where the robot manipulates the base of the needle, which, for a long needle, can be 10 cm. or even more from the entry point at the tip of the needle. The workspace can be as little as the order of 10 millimeters as opposed to several centimeters for the prior art systems. In the systems described in this application, the longitudinal needle motion is mechanically separated from the lateral manipulations of the needle. A characteristic of these implementations of the devices of this disclosure is that the needle driving mechanism is capable of driving needles of variable lengths while the dimensions and workspace of the driving mechanism does not depend on the length of the needles. In prior art systems, the longitudinal needle insertion is either not available robotically, or if available, it requires the manipulator to have a range of motion at least as long as the length of insertion of the needle.

Examples of needle base driving and needle shaft driving will be shown below by a numerical simulation. A smaller workspace allows the use of a smaller robot which is advantageous in such medical applications. Such a workspace of only 10 millimeters or so is advantageous from a safety point of view. The robot is then incapable of accidentally moving significantly and of injuring neighboring organs.

Because of their low profile, the robotic needle manipulators described in this application can be easily placed on the patient's body, which is also advantageous because this compensates for patient motion during the procedure—the robot moves with the patient. The robot can be placed on the patient directly and be connected with belts, or adhesives, thereby affixing its lateral position on the patient's skin.

Furthermore, the low profile enables the robotic needle manipulator to be used more readily in the limited space of a CT or other three-dimensional imaging system.

According to an exemplary aspect of the present invention, the robotic needle manipulator is supported by a semi-active support arm whose purposes may be one or more of the following:
(i) to append the robotic needle manipulator to the patient's body surface by applying a gentle force, and
(ii) to track the robot position in real-time.

The semi-active arm may have 3 or more degrees of freedom, and preferably 6, in order to be able to laterally locate the robot above the needle entry point and to orient the robot plane relative to the patient's body. The semi-active arm may comprise a series of links connected by joints, as in a serial robot. However, it is to be understood that a parallel robot or a hybrid serial-parallel robot may also be used in this application. For a serial robot, each such semi-active joint should have an encoder which monitors the rotation of the joint, so that the position and orientation of the end effector can be calculated by solution of the forward kinematics problem. The semi-active arm can, on the other hand, alternatively be fully passive, meaning that there are no motors in the joints and the joints can be rotated freely unlocked, or there may be motors or springs operating on one or more joints so that the angle of at least one joint can be controlled. Alternatively, one or more joints can be locked and others passive. Regardless of the actual configuration used, the encoders on the joints, if fitted, can be used as the sensors for determining the position of the semi-active arm relative to the patient's body, hence determining the position and orientation of the robot, such as for the purposes of the registration described herewithin.

Control of one or more joints is useful for solution of the respiration gait problem (respiration compensation), where the robot should move synchronously with movements of the patient's body. An additional function of the semi-active arm may be to monitor the respiration of the patient. The semi-active arm reduces the need for placing external sensors on the patient's skin, as is done in prior art methods, in order to monitor the stages of the breath cycle of the patient. Since the robotic needle manipulator maintains contact with the patient's chest, its sensors are able to define the breath cycle of the patient.

A particularly useful configuration of the support arm is to provide it with positive control in the direction perpendicular to the patient's body surface, such as by use of a spring, such that it exerts sufficient pressure that the robotic needle manipulator remains in contact with the patient's skin, yet allows the robotic needle manipulator to rise and fall with the patient's breathing cycle. At the same time, the other directions of freedom of the robotic needle manipulator control system may advantageously be maintained sufficiently stiffly controlled that the robotic needle manipulator remains nominally constrained by the support arm to its predetermined position on the subject's body at the needle insertion point, yet allows some level of freedom of movement should the patient move laterally during the procedure due to coughing or discomfort or the like.

Additionally, the need for sensors on the semi-active arm may be dictated by the need to maintain registration of the robot position with the CT coordinate system. The initial robotic registration to establish correct co-ordinate transformation between the robot and CT systems, becomes invalidated by the patient's breathing motion, which also moves the robot. The sensors in the semi-active arm are able to track the robot position, in order to maintain the correct current co-ordinate transformation from the initial registration procedure, even as the robot moves.

An additional advantage of connecting the robot via a semi-active arm is that the arm with the robot and the patient now move together and it is possible to perform volume scans of the patient with the needle inserted. In order to perform a volume scan, the CT bed needs to move. When the needle is inside the patient and the CT bed moves, the needle and the robot move with the bed and the patient, so there is no relative movement between the needle and the patient.

There is thus provided in accordance with an exemplary implementation of the devices described in this disclosure, a system for needle insertion into a subject, comprising:
(i) a robotic platform having a plurality of degrees of freedom providing the needle with a desired pose, and (ii) a needle gripper attached to the robotic platform, the needle gripper being activated to provide motion to the needle in its longitudinal direction,
wherein the needle gripper grips the shaft of the needle distally to the base of the needle.

Such a system may further comprise a positioning system for positioning the robotic platform close to the point of insertion of the needle into the subject. Furthermore, the needle gripper may comprise at least a pair of rollers on either side of the needle, such that co-ordinated rotation of the rollers causes the needle to move in its longitudinal direction. Additionally, a needle rotation mechanism may be incorporated, such that the needle can be rotated about its axis. In yet other implementations, the needle gripper may be adapted to release its grip on the needle, such that the needle can move longitudinally freely.

In yet other implementations of the needle insertion systems of the present application, the robotic platform may comprise a base plate, such that the robotic platform can be positioned with the base plate in juxtaposition to the skin of the subject. Furthermore, the pose may be adjusted in co-ordination with activation of the needle gripper such that the orientation of the needle can be adjusted as the needle is inserted into the subject.

Furthermore, in any of the above-described systems, gripping of the needle shaft distally to the needle base is such that the system can operate without any part thereof extending further from the subject than the base of the needle. In some exemplary implementations, the workspace of the system may not extend more than 50 mm from the point of insertion of the needle, and in other implementations not more than 30 mm. and in yet other implementations, not more than 20 mm.

In any of the above-described systems, the robotic platform may be a parallel, a serial or a hybrid robotic platform.

There is further provided in accordance with another exemplary implementation of the devices described in this disclosure, a system for needle insertion into a subject, comprising:
(i) a robotic platform for aligning and inserting the needle into the subject,
(ii) a support arm for aligning the robotic platform close to the point of insertion of the needle into the subject, and
(iii) a sensor system for detecting motion of the body of the subject close to the point of insertion of the needle,
wherein the sensor system provides commands for the robotic platform, for insertion of the needle in co-ordination with the detected motion of the body of the subject.

The motion of the body of the subject mentioned hereinabove in relation to such a system, may be breathing related motion. Additionally, the support arm may be designed to apply pressure on the robotic platform, such that the robotic platform remains in contact with the subject's body, and the support arm may be such that its motion is essentially unconstrained in a direction perpendicular to the surface of the patient's body, such that the robotic platform moves freely with motion of the subject's body. Furthermore, the motion of the support arm may be partially constrained in directions parallel to the surface of the patient's body, such that the robotic platform is generally constrained by the support arm to a predetermined position on the subject's body.

Yet other implementations perform a method for insertion a needle into a subject, comprising:
(i) providing a robotic platform having a plurality of degrees of freedom to align the needle at its desired pose,
(ii) providing a needle gripper for attachment to the robotic platform,
(iii) using the needle gripper to grip the shaft of the needle distally from the base of the needle, and
(iv) activating the needle gripper to provide motion to the needle in its longitudinal direction.

An additional exemplary method for inserting a needle into a subject, may comprise:
(i) providing a robotic platform for aligning the needle for insertion into the subject,
(ii) providing a support arm for aligning the robotic platform close to the point of insertion of the needle into the subject,
(iii) detecting motion of the body of the subject close to the point of insertion of the needle, and
(iv) using the detected motion of the body to provide commands for the robotic platform, such that the needle can be inserted in co-ordination with the detected motion of the body of the subject.

BRIEF DESCRIPTION OF THE DRAWINGS

The present invention will be understood and appreciated more fully from the following detailed description, taken in conjunction with the drawings in which.

DETAILED DESCRIPTION

Figure 1:
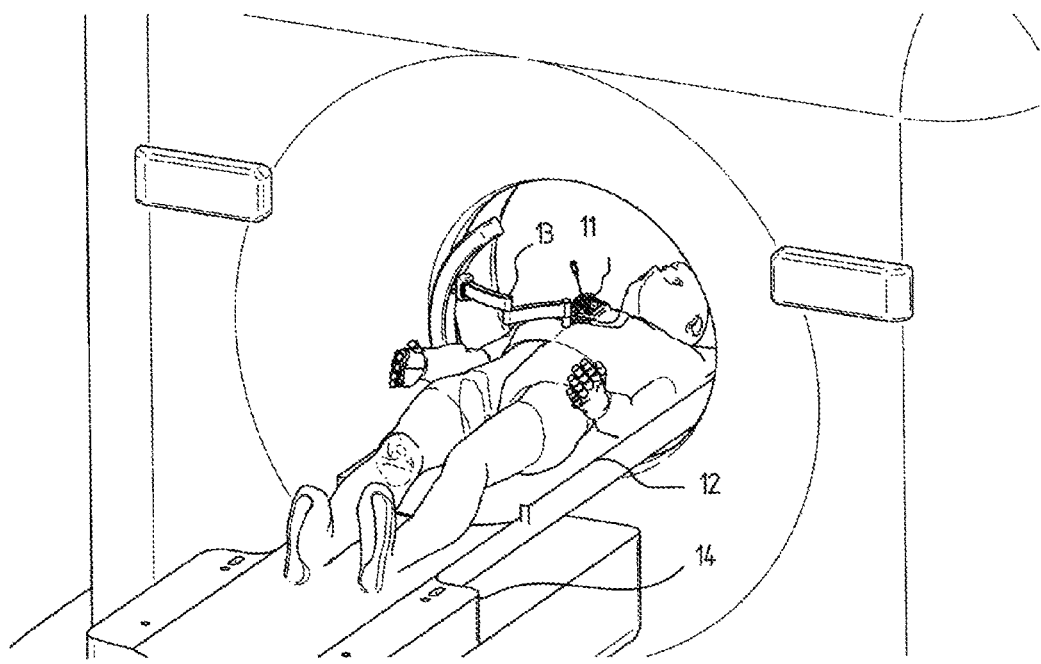
FIG. 1 shows overall view of a system of the present disclosure, used to manipulate a needle under the guidance of a CT imaging system.
Figure 2:
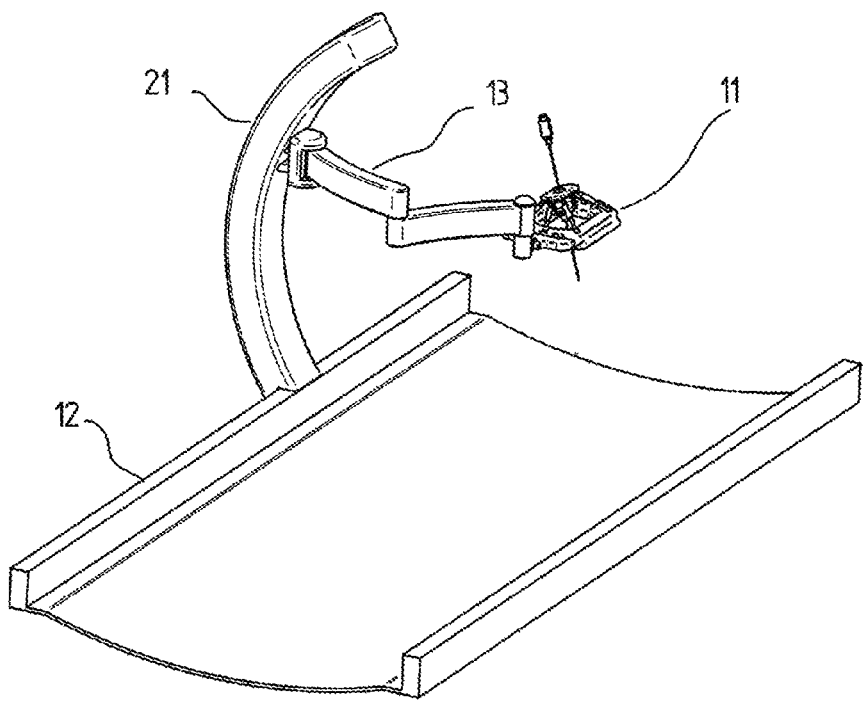
FIG. 2 is a schematic view of the robotic needle manipulator attached to the patient base plate for insertion into an imaging system.

Reference is first made to FIGS. 1 and 2 which show the overall view of a system used to manipulate the needle under the guidance of an imaging system, such as CT or MRI guidance. However, it is to be understood that the needle steering manipulation technique and the needle manipulating robot is not limited to use with CT or MRI imaging modality, but can be used with any existing imaging modality such as Ultrasound, PET, or the like.

FIG. 1 shows an exemplary system mounted on a CT system. The system does not need to be connected to the CT system directly. The robotic needle manipulator 11 may be connected to the base element plate 12 via a semi-active arm 13, which may be connected to the base element via an arched support arm 21. The base element may be placed on the imaging system bed 14 and moves together with the imaging system bed. Alternatively, the support arch could be mounted directly on the imaging system bed.

Reference is now made to FIG. 2 where the complete system is shown without the CT. The miniature robot 11 is shown connected to the base element 12 via a semi-active arm 13. The semi-active arm is so-called because it has one or more actuators, but does not generally need as many actuators as its number of degrees of freedom, such that not all of the joints need to be controlled. That would make the arm unnecessarily complex and costly for its function, which is only to position the robotic needle manipulator in the correct position relative to the needle entry point and the patient's body pose. The base element, preferably having the shape of the CT-bed, should be stiff enough so that the patient can lie on it and firm enough that the connection of the arched support arm 21 to it will be rigid enough.

In the example shown, the semi-active arm has 5 degrees of freedom, 3 for positioning of the base of the robotic needle manipulator anywhere on the patient's body, and 2 for orienting of the robotic needle manipulator to be generally parallel to the patient's body, and advantageously in contact with the subject's skin.

Figure 3:
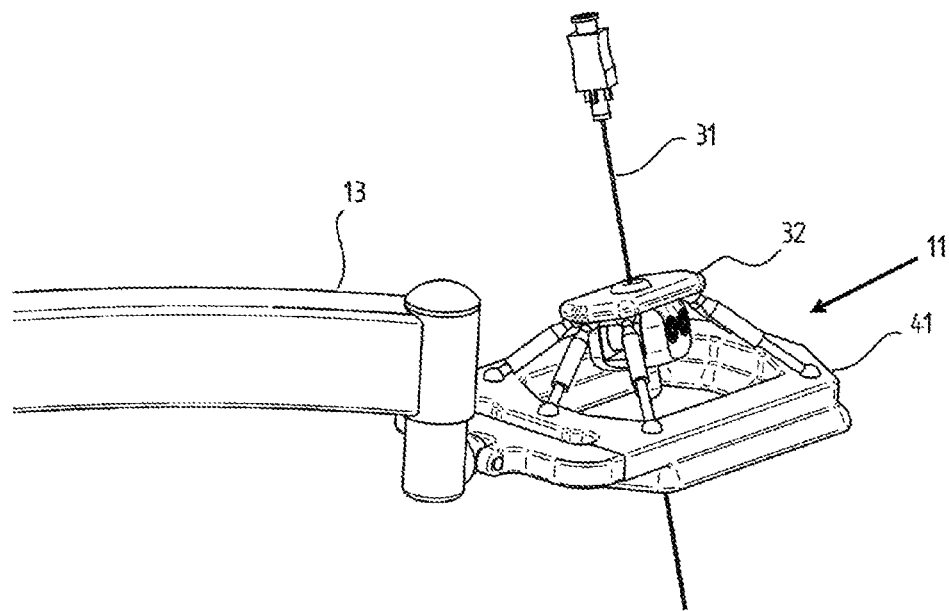
FIG. 3 is a schematic view of a complete robotic needle manipulator shown holding a needle remotely from the needle base.

Reference is now made to FIG. 3 where a complete robotic needle manipulator is shown. A robot 11 is shown holding the needle 31. For purposes of illustration, the robot is based on the well-known Stewart-Gough platform, which was introduced in 1965, though it is to be understood that this is just an exemplary implementation, and any other suitable type of robot could be used. The robot has 6 degrees-of-freedom and can position and orient the needle cannula in space by appropriately positioning and orienting the actuated platform 32 of the robot relative to its base plate 41. Inside the robotic needle manipulator, there is a needle driving mechanism to be described in FIGS. 5 and 6. The base plate 41 of the robotic needle manipulator may be connected to the semi-active arm 13 by spherical or U-joints enabling orientation of the device on the skin of the patient.

Figure 4:
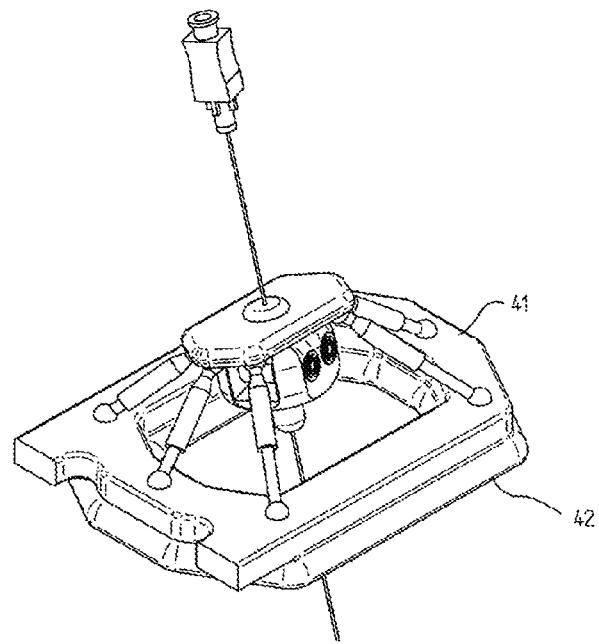
FIG. 4 is another schematic view of the robotic needle manipulator of FIG. 3.
Figure 5:
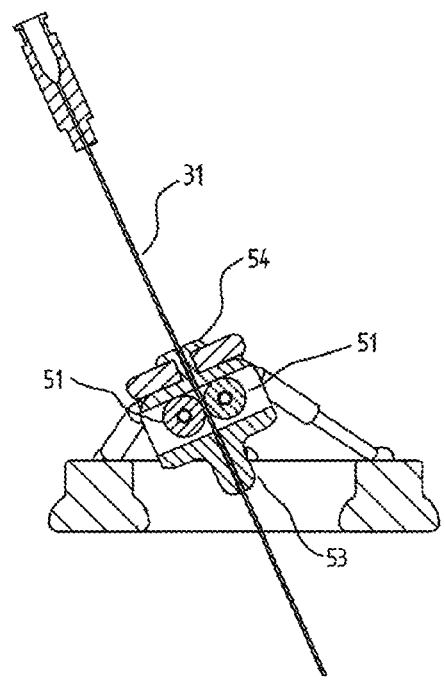
FIGS. 5 and 6 show schematically a complete robotic needle manipulator at two different insertion angles, incorporating a needle driving mechanism employing rotation of two or more rollers, such that the needle insertion can be performed under robotic control.

Reference is now made to FIG. 4 where the modified Stewart-Gough platform is shown in close up. The base plate 41 is placed on the patient's skin. The base may have a soft pillow 42 to conform to the body of the patient. Although FIGS. 4 and 5 show a 6-DOF modified Stewart-Gough robot, it is to be understood that the robotic needle manipulator could utilize any suitable type of robotic platform, whether parallel, such as the Stewart-Gough, or serial, or hybrid.

Figure 6:
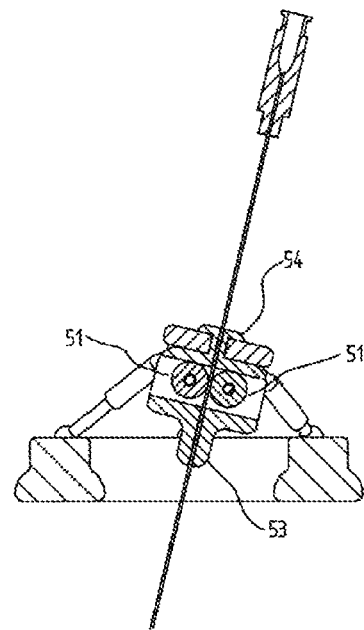

The robotic needle manipulator shown in FIGS. 1 to 4 may be used either as a simple robotic needle positioning and orientating device, such as could be used by the physician for manual insertion of the needle, or it could incorporate a needle driving mechanism, such that the needle insertion too could be performed under robotic control. Reference is now made to FIG. 5 and FIG. 6 where an example of such a needle driving mechanism is shown in two different insertion orientation angles, employing rotation of two or more rollers 51. The driving force is created by non-sliding friction between the needle shaft 31 and the rollers 51. After passing the rollers the needle is traversed through a directing cannula 53, which more precisely controls the direction of the exiting needle. Also shown schematically in FIGS. 5 and 6 is a needle rotation mechanism 54. This mechanism could be based on a pair of friction rollers aligned with their axes in the plane essentially parallel to the shaft of the needle, or on a single driven pulley wheel in that plane, with the needle shaft passing through a friction clutch at its center, such that application of the clutch and rotation of the pulley wheel will rotate the needle, or by any other of the known mechanisms for providing such selectable rotation motion. Any such rotation mechanism must allow free longitudinal motion of the needle when an insertion step is actuated.

Figure 7:
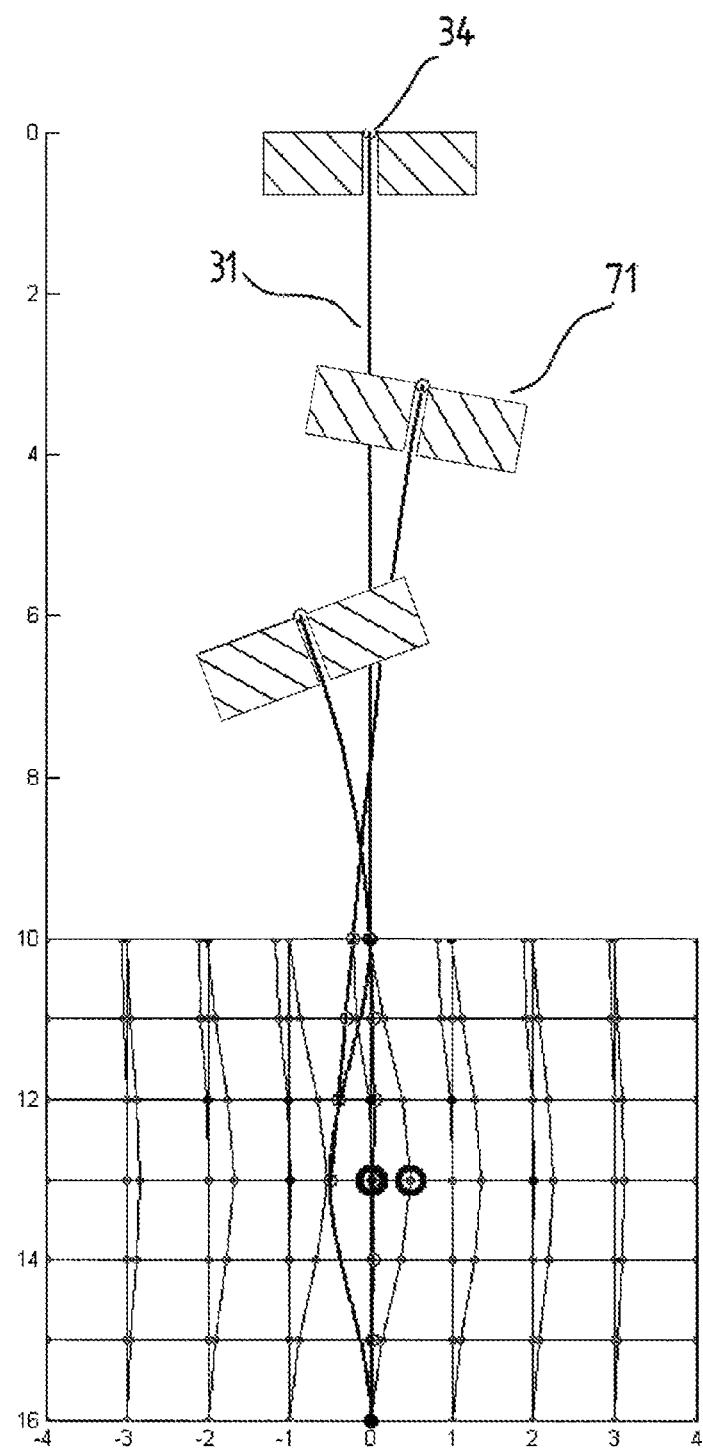
FIG. 7 is a graphical representation of a prior art example of needle steering by steering of the needle base.

Reference is now made to FIG. 7 where a spatial simulation of a prior art example of needle steering by steering of the needle base is shown. The simulation is based on the system described in PCT published application WO 2007/141784 A2. The axes, which represent the longitudinal and lateral views of the needle environment, are marked in cm. The needle holder 71 holds the base 34 of the needle 31 and manipulates the base of the needle as shown. It can be seen that the workspace required for the robot manipulator to insert the needle has to be at least the height of the needle. For instance, to insert the needle 6 cm into the subject's body, the workspace of the robot manipulator has to be at least 6 cm in length and, for the orientation manipulations shown in the simulation of FIG. 7, about 5-6 cm in width, which is the extent of lateral travel of the needle base 34. In medical applications, a robot having a large workspace is disadvantageous because of safety issues. Large workspace means that the robot can move accidently to the wrong place.

Figure 8:
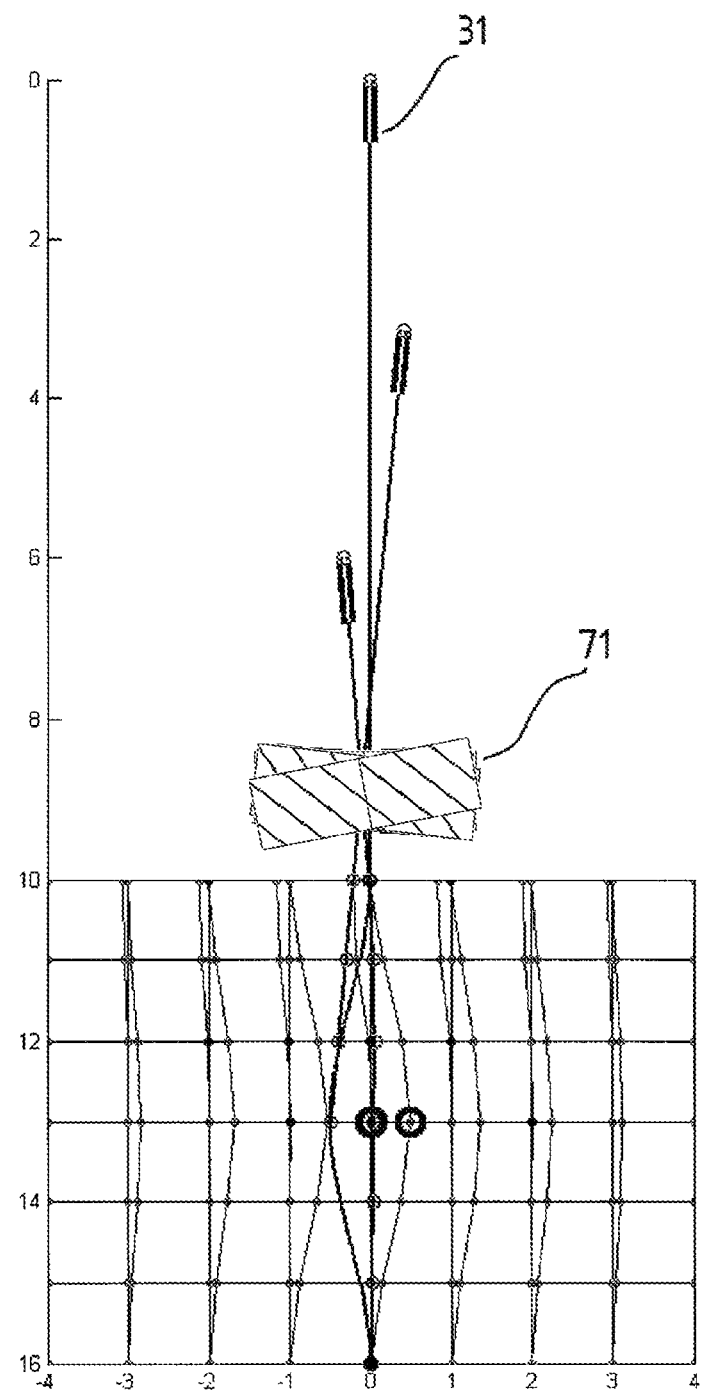
FIG. 8 is a graphical representation of an example of needle steering using the distal shaft gripping method of the present disclosure, showing the space saving advantages over the prior art method shown in FIG. 7.

Reference is now made to FIG. 8 where there is shown an example of needle steering by manipulation of its shaft using the robotic needle manipulator of the present application. The needle is required to realize the same trajectory as in FIG. 7, but it can be seen that the robot manipulator workspace required is much smaller, because the manipulator is very close to the skin. In the example shown the workspace is seen to be only 2 cm. high, and the width approximately 3 cm. The height is dependent on the type of robot used, but typical robots of height even up to 5 cm. still show a workspace advantage over the prior art methods of robotic needle insertion. Robots made for such a small workspace have a significant advantage relating to safety since the manipulator is physically constrained to small area and cannot harm the nearby areas. Furthermore, the decoupling of the position and orientation manipulation mechanisms from the pushing mechanism also contributes to increased safety. Additionally, the workspace of the robot is flat or planar and doesn't depend on the needle length. The same robot can accommodate needles of effectively any practically used length. Furthermore, the robot can be more easily accommodated in the limited confines of a tomographic imaging system.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

What is claimed is:

1. A robotic needle manipulator for steering a needle within soft tissue of the subject by manipulating a shaft of the needle at its distal end, comprising:

a robotic platform having a plurality of degrees of freedom; and a needle gripper configured to be attached to the robotic platform and to grip the needle, the needle gripper comprising a needle driving mechanism configured to provide insertion motion to the needle in a longitudinal direction of the needle, wherein coordinated activation of the robotic platform and the needle driving mechanism results in adjustment of the orientation angle of the needle inside the soft tissue of the subject during insertion motion of the needle in the longitudinal direction, such that the needle traverses a non-linear path within the soft tissue of the subject.

2. The robotic needle manipulator of claim 1, wherein the attachment of the needle gripper to the robotic platform is such that upon coupling the needle to the needle gripper, the needle driving mechanism is positioned at the distal end of the needle shaft.

3. The robotic needle manipulator of claim 1, wherein the needle driving mechanism comprises at least a pair of rollers on either side of the needle, such that coordinated rotation of the rollers causes the needle to move in the longitudinal direction.

4. The robotic needle manipulator of claim 1, wherein the robotic platform comprises an actuated platform and a base plate, the base plate being configured for positioning on the subject.

5. The robotic needle manipulator of claim 4, further comprising a positioning system configured for positioning the base plate close to a point of insertion of the needle into the body of the subject.

6. The robotic needle manipulator of claim 1, further comprising a needle rotation mechanism configured to rotate the needle about its axis.

7. The robotic needle manipulator of claim 1, further comprising a sensor system for detecting motion of the body of the subject.

8. The robotic needle manipulator of claim 7, wherein the sensor system is configured to define a breath cycle of the subject.

9. A robotic needle manipulator for steering a needle within soft tissue of the subject by manipulating a shaft of the needle at its distal end, comprising:
 a robotic platform comprising an actuated platform having a plurality of degrees of freedom; and
 a needle gripper configured to be attached to the actuated platform and to provide insertion motion to the needle in a longitudinal direction of the needle,
 wherein the actuated platform and the needle gripper are configured to be activated in coordination, such that the coordinated activation of the actuated platform and the needle gripper enables adjustment of the orientation angle of the needle inside the soft tissue of the subject during insertion motion of the needle within the soft tissue of the subject.

10. The robotic needle manipulator of claim 9, wherein the robotic platform further comprises a base plate configured for positioning on the subject.

11. The robotic needle manipulator of claim 10, wherein the robotic platform is adapted to position and orient the needle in space by appropriately positioning and orienting the actuated platform relative to the base plate to achieve a desired pose of the needle.

12. The robotic needle manipulator of claim 9, wherein the needle gripper comprises a needle driving mechanism configured to provide the insertion motion to the needle in a longitudinal direction.

13. The robotic needle manipulator of claim 12, wherein the needle driving mechanism comprises at least a pair of rollers on either side of the needle, such that coordinated rotation of the rollers causes the needle to move in the longitudinal direction.

14. The robotic needle manipulator of claim 12, wherein the attachment of the needle gripper to the actuated platform is such that upon coupling the needle to the needle gripper, the needle driving mechanism is positioned at the distal end of the needle shaft.

15. The robotic needle manipulator of claim 9, further comprising a semi-active support arm configured to align the robotic platform close to a point of insertion of the needle into a body of the subject.

16. The robotic needle manipulator of claim 15, wherein the semi-active support arm is configured to apply pressure to the robotic platform, such that the robotic platform remains in contact with the body of the subject.

17. The robotic needle manipulator of claim 15, wherein the semi-active support arm is configured such that its motion is essentially unconstrained in a direction perpendicular to a surface of the body of the subject, such that the robotic platform moves freely with motion of the body of the subject.

18. The robotic needle manipulator of claim 15, wherein the semi-active support arm is configured to constrain the robotic platform to a predetermined position on the body of the subject.

* * * * *